United States Patent
Sembo et al.

(10) Patent No.: US 6,555,092 B2
(45) Date of Patent: Apr. 29, 2003

(54) PESTICIDAL AEROSOL COMPOSITIONS AND PESTICIDAL METHODS

(75) Inventors: Satoshi Sembo, Nishinomiya (JP); Yasuyori Tanaka, Toyonaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/946,546

(22) Filed: Sep. 6, 2001

(65) Prior Publication Data

US 2002/0052406 A1 May 2, 2002

(30) Foreign Application Priority Data

Sep. 8, 2000 (JP) .................................. 2000-272865

(51) Int. Cl.$^7$ .............................................. A01N 25/06
(52) U.S. Cl. ................ 424/45; 424/405; 424/DIG. 10; 514/471; 514/919
(58) Field of Search ........................... 424/45, 47, 405, 424/DIG. 10; 514/919, 471

(56) References Cited

U.S. PATENT DOCUMENTS

| 2,524,590 A | * | 10/1950 | Boe | .................. | 252/305 |
| 5,434,181 A | * | 7/1995 | Kodaka et al. | ............. | 574/471 |
| 5,532,365 A | * | 7/1996 | Kodaka et al. | ............. | 544/212 |

* cited by examiner

*Primary Examiner*—Neil S. Levy
(74) *Attorney, Agent, or Firm*—Birch, Stewart, Kolasch & Birch, LLP

(57) ABSTRACT

The present invention provides pesticidal aerosol compositions and pesticidal methods. The pesticidal aerosol compositions comprise a propellant, 1-methyl-2-nitro-3-[(3-tetrahydrofuryl)methyl]guanidine and N-methyl-2-pyrrolidone, wherein a weight to weight ratio of said 1-methyl-2-nitro-3-[(3-tetrahydrofuryl)methyl]guanidine to said N-methyl-2-pyrrolidone is at a pesticidally synergistic weight to weight ratio. The pesticidal methods comprise applying to a pest or to a habitat of a pest, at least one the pesticidal aerosol compositions.

6 Claims, No Drawings

PESTICIDAL AEROSOL COMPOSITIONS AND PESTICIDAL METHODS

TECHNICAL FIELD OF THE INVENTION

The present invention relates to pesticidal aerosol compositions or pesticidal methods.

BACKGROUND ARTS

U.S. Pat. No. 5,532,365 describes 1-methyl-2-nitro-3-[(3-tetrahydrofuryl)methyl]guanidine as a pesticidal compound and describes pesticidal compositions comprising 1-methyl-2-nitro-3-[(3-tetrahydrofuryl)methyl]guanidine and a carrier. Such pesticidal compositions are insufficient to provide an effective pesticidal effect and knockdown effect when sprayed onto a household pest or habitat of said household pest.

SUMMARY OF THE INVENTION

The present invention provides pesticidal aerosol compositions and pesticidal methods. The pesticidal aerosol compositions comprise a propellant, 1-methyl-2-nitro-3-[(3-tetrahydrofuryl)methyl]guanidine and N-methyl-2-pyrrolidone, wherein a weight to weight ratio of said 1-methyl-2-nitro-3-[(3-tetrahydrofuryl)methyl]guanidine to said N-methyl-2-pyrrolidone is at a pesticidally synergistic weight to weight ratio. The pesticidal methods comprise applying to a pest or to a habitat of a pest, at least one the pesticidal aerosol compositions.

DETAILED DESCRIPTION OF THE INVENTION

The pesticidal aerosol compositions of the present invention comprise a propellant, 1-methyl-2-nitro-3-[(3-tetrahydrofuryl)methyl]guanidine and N-methyl-2-pyrrolidone. The weight to weight ratio of 1-methyl-2-nitro-3-[(3-tetrahydrofuryl)methyl]guanidine to N-methyl-2-pyrrolidone in the pesticidal aerosol compositions is usually from 2:1 to 1:999, or from 1:1 to 1:999, or from 1:1 to 1:100.

Typically, 0.01 to 10% by weight of 1-methyl-2-nitro-3-[(3-tetrahydrofuryl)methyl]guanidine is utilized in the pesticidal aerosol compositions, but the amount thereof in the pesticidal aerosol compositions may vary upon the form use. Alternatively, 0.0005 to 30% by weight of N-methyl-2-pyrrolidone may be utilized in the pesticidal aerosol compositions. Said weight percentages above of 1-methyl-2-nitro-3-[(3-tetrahydrofuryl)methyl]guanidine and N-methyl-2-pyrrolidone are based on the total weight of the provided pesticidal aerosol composition.

As examples of the propellant in the pesticidal aerosol compositions, there is mentioned dimethyl ether, propane, isobutene and the like, and mixture thereof. When utilizing the mixture of propellants, the mixture may comprise at least 30% by weight of dimethyl ether and another propellant, or may comprise at least 50% by weight of dimethyl ether and another propellant, or may essentially consist of dimethyl ether, wherein said weight percentages are based on the total weight of the provided propellant. In the pesticidal aerosol compositions, 10 to 90% by weight of the propellant may be utilized therein, wherein said weight percentage is based on the total weight of the provided pesticidal aerosol composition. When producing a pesticidal aerosol composition that releases at once all of the pesticidal aerosol composition, i.e., a total release aerosol, 70 to 90% by weight of the propellant may be utilized therein, wherein said weight percentage is based on the total weight of the provided pesticidal aerosol composition.

As needed, the pesticidal aerosol compositions may additionally comprise a solvent. As examples of such a solvent, there is mentioned alcohols such as methyl alcohol, ethyl alcohol, isopropyl alcohol and benzyl alcohol; glycols such as ethylene glycol, diethylene glycol, propylene glycol, polyethylene glycol and polypropylene glycol; glycol monoether such as diethylene glycol monomethyl ether, diethylene glycol monoethyl ether, diethylene glycol monobutyl ether, propylene glycol monomethyl ether, propylene glycol monoethyl ether and ethylene glycol monophenyl ether; aromatic or aliphatic hydrocarbons such as xylene, toluene, kerosene, gas oil and hexane; propylene carbonate; water and the like. When utilized, the amount of the solvent in the pesticidal aerosol compositions may be 80% by weight or less or 50% by weight or less, wherein said weight percentage is based on the total weight of the provided pesticidal aerosol composition.

Further, in the pesticidal aerosol compositions, there may also be utilized therein an anti-oxidant, emulsifier, other pesticidal compound, pest repellent compound, synergist or the like.

As examples of the anti-oxidant, there are mentioned BHT, BHA and the like.

As examples of the emulsifier, there are mentioned non-ionic emulsifiers such as polyoxyethylene fatty acid ester, glycerin fatty acid ester and sorbitan fatty acid ester and the like.

a pest repellent,

As examples of the other pesticidal compound, there are mentioned pyrethroid compounds such as pyrethroid compounds such as allethrin, tetramethrin, prallethrin, phenothrin, resmethrin, cyphenothrin, permethrin, cypermethrin, deltamethrin, tralomethrin, cyfluthrin, furamethrin, imiprothrin, etofenprox, fenvalerate, fenpropathrin, silafluofen, bifenthrin and transfluthrin; organophosphorus compounds such as dichlorvos, fenitrothion, tetrachlorvinphos, fenthion, chlorpyrifos and diazinon; carbamate compounds such as propoxur, carbaryl, metoxadiazone and fenobucarb; chitin synthesis inhibitors such as lufenuron, chlorfluazuron, hexaflumuron, diflubenzuron, cyromazine, triflumuron, teflubenzuron, flufenoxuron, fluazuron, triazamate and 1-(2,6-difluorobenzoyl)-3-[2-fluoro-4-(1,1,2,3,3,3-hexafluoropropoxy)phenyl]urea; juvenile hormone analogues such as pyriproxyfen, methoprene, hydroprene and fenoxycarb; neonicotinoid compounds such as acetamiprid, nitenpyram, thiacloprid, thiamethoxam and nitroiminohexahydro-1,3,5-triazine derivatives; N-phenylpyrazole compounds and the like.

As examples of the pest repellant compound, there are mentioned N,N-diethyl-m-toluamide, limonene, linalool, citronellol, menthol, menthone, hinokitiol, geraniol, eucalyptol, indoxacarb, carane-3,4-diol and the like.

As examples of the synergist, for example, there are mentioned PBO, MGK264, S421, IBTA and the like.

The present invention compositions can be produced as follows.

Typically, 1-methyl-2-nitro-3-[(3-tetrahydrofuryl)methyl]guanidine, N-methyl-2-pyrrolidone and the propellant are mixed together to produce the pesticidal aerosol compositions. For example, 1-methyl-2-nitro-3-[(3-tetrahydrofuryl)methyl]guanidine and N-methyl-2-pyrrolidone are mixed together into a solution such as by stirring together 1-methyl-2-nitro-3-[(3-tetrahydrofuryl)methyl]guanidine and N-methyl-2-pyrrolidone. The mixture can then be packed into an aerosol container, to which there may be added the solvent, anti-oxidant, emulsifier, other pesticidal compound, pest repellent compound, synergist or the like. An aerosol valve is then attached to said aerosol container. The propellant is then packed through the stem into the aerosol container. After shaking contents in the aerosol container, an actuator is added to the aerosol container to provide a pesticidal aerosol composition of the present invention. When producing the total release pesticidal aerosol compositions, a total release actuator is usually added to the aerosol container.

To control pests with the pesticidal aerosol compositions, the pesticidal aerosol composition can be applied to the pest or to the habitat of the pest. In such cases, the pesticidal aerosol compositions can be sprayed directly onto the pest or sprayed onto a habitat of the pest. Typically, such habitats of pests involve locations found in the household or locations in the proximity of the household. For example, such habitats of the pest may include a plant, soil or the like.

When applying the pesticidal aerosol compositions, the application amount thereof may vary, depending on the type of the pest or on the environmental factors at location of application. In general, the pesticidal aerosol compositions are applied to the pest or habitat of the pest in an amount, such that 0.1 to 1000 mg of 1-methyl-2-nitro-3-[(3-tetrahydrofuryl)methyl]guanidine is applied to 1 $m^2$ of the application location. Such an application amount usually is employed when applying the pesticidal aerosol compositions to cover a 2-dimentional area of said habitat of the pest. When applying the pesticidal aerosol compositions to cover a 3-dimentional volume, the pesticidal aerosol compositions can be applied to the habitat of the pest or pest in an amount, such that 0.1 to 300 mg of 1-methyl-2-nitro-3-[(3-tetrahydrofuryl)methyl]guanidine is applied to 1 $m^3$ of the application location.

The pesticidal aerosol compositions are effective with various pests, such as with arthropods typically found in the household or in the close proximity thereof. Examples of such pests include the following:

Hemiptera: plant hoppers (Delphacidae) such as small brown plant hopper (*Laodelphax striatellus*), brown plant hopper (*Nilaparvata lugens*) and white-backed rice hopper (*Sogatella furifera*); leafhoppers (Deltocephalidae) such as green rice leafhopper (*Nephotettix cincticeps*) and green rice leafhopper (*Nephotettix virescens*); aphids (Aphididae) such as cotton aphid (*Aphis gossypii*) and green peach aphid (*Myzus persicae*); plant bugs (Heteroptera) such as green rice bug (*Nezara antennata*) and bean bug (*Riptortus clavetus*) and the like.

Lepidoptera: Pyralidae such as Indian meal moth (*Plodia interpunctella*); tiger moths (Arctiidae) such as fall webworm (*Hyphantria cunea*); clothes moths such as casemaking clothes moth (*Tinea translucens*) and webbing clothes moth (*Tineola bisselliella*) and the like;

Diptera: mosquitoes (Culicidae) such as common mosquito (*Culex pipiens pallens*), *Culex tritaeniorhynchus* and *Culex quinquefasciatus*; Aedes sp. such as yellow fever mosquito (*Aedes aegypti*) and *Aedes albopictus*; Anopheles sp. such as *Anopheles sinensis*; Chironomidae (midges); muscid flies (Muscidae) such as housefly (*Musca domestica*) and false housefly (*Muscina stabulans*); blow flies (Calliphoridae); flesh flies (Sarcophagidae); little housefly (*Fannia canicularis*); Anthomyiidae such as seedcorn maggots (*Delia platura*) and onion maggot (*Delia antiqua*); fruit flies (Tephritidae); vinegar flies (Drosophilidae); moth flies (Psychodidae); black flies (Simuliidae); breeze flies (Tabanidae); stable flies (Stomoxyidae); laef miner flies (Agromyzidae) and the like.

Beetles (Coleoptera): weevils (Curculionidae) such as ricewater weevil (*Lissorhoptrus oryzophilus*) and adzuki bean weevil (*Collosobruchus chinensis*); corn rootworms such as western corn rootworm (*Diabrotica virgifera*) and southern corn rootworm (*Diabrotica undecimpunctata howardi*); scarabs (Scarabaeidae) such as cupreous chafer (*Anomala cuprea*) and soybean beetle (*Anomala rufocuprea*); Tenebrionidae (darkling beetles) such as red flour beetle (*Tribolium castaneum*); Epilachna sp. such as deathwatch beetles (Anobiidae); powderpost beetles (Lyctidae); false powderpost beetles (Bostrychidae) and the like.

Cockroaches (Blattidae): German cockroach (*Blattella germanica*), smokybrown cockroach (*Periplaneta fuliginosa*), American cockroach (*Periplaneta americana*), brown cockroach (*Periplaneta brunnea*), oriental cockroach (*Blatta orientalis*) and the like.

Hymenoptera: ants (Formicidae), hornets (Vespidae), Bethylid wasp (Bethylidae) and the like.

Termites (Isoptera): *Reticulitermes speratus*, Formosan subterranean termite (*Coptotermes formosanus*) and the like.

In particular, the pesticidal aerosol compositions are well suited for controlling household pests such as flies, mosquitoes, cockroaches, termites and the like.

EXAMPLES

Hereinafter, the present invention is described in more detail with the examples, but the present invention is not limited thereto.

FORMULATION EXAMPLES 1 to 3

Five-hundredths (0.05) grams of 1-methyl-2-nitro-3-[(3-tetrahydrofuryl)methyl]guanidine was dissolved, respectively, in particular amounts of N-methyl-2-pyrrolidone shown in Table 1 below (i.e., 0.15 g, 0.5 g and 2.0).

TABLE 1

| Formulation Example | Amount of N-methyl-2-pyrrolidone |
| --- | --- |
| Formulation example 1 | 0.15 g |
| Formulation example 2 | 0.50 g |
| Formulation example 3 | 2.0 g |

The mixtures were each inserted into an 180 ml aerosol container. A saturated hydrocarbon solvent (Isopar G, Exxon Chemical Company) was added each of the mixtures, to have each of the mixtures amount to 30.0 g. After attaching aerosol valves to the aerosol containers, 20.0 g of dimethylether was packed into each of the aerosol containers. After shaking the contents in each of the aerosol containers, an actuator was added each of the aerosol containers to produce formulations 1, 2 and 3, respectively.

FORMULATION EXAMPLES 4 and 5

N-methyl-2-pyrrolidone is added and dissolved, respectively, into a mixture containing 0.3 g of 1-methyl-2-nitro-3-[(3-tetrahydrofuryl)methyl]guanidine and 0.6 g of another pesticidal compound to amount to 7.5 g. Said another pesticidal compound is shown in Table 2 below.

TABLE 2

| Formulation Example | said another pesticidal compound |
| --- | --- |
| Formulation example 4 | d-phenothrin |
| Formulation example 5 | d.d-T-cyphenothrin |

Five (5.0) grams water was added to each of the mixtures. The mixtures were each inserted into an 180 ml aerosol container. After attaching aerosol valves to the aerosol containers, 37.5 g of dimethyl ether were packed into each of the aerosol containers. After shaking the contents in each of the aerosol containers, an actuator was added each of the aerosol containers to produce the formulations 4 and 5, respectively.

COMPARATIVE EXAMPLE 1

Five-hundredths (0.5) grams of 1-methyl-2-nitro-3-[(3-tetrahydrofuryl)methyl]guanidine was inserted into an 180 ml aerosol container. A saturated hydrocarbon solvent (Isopar G, Exxon Chemical Company) was then added thereto to amount to 30.0 g. After attaching an aerosol valve to the aerosol container, 20.0 g of dimethyl ether were packed into the aerosol container. After shaking the contents in the aerosol container, an actuator was added to the aerosol containers to produce a comparative formulation.

TEST EXAMPLE

A plastic container (diameter 13 cm, height 10 cm, bottom area a 32 mesh screen) to which 10 adult German cockroaches (5 male and 5 female) have been added is placed on the bottom area in a glass cylinder (diameter 20 cm and height of 60 cm). From the top area of the glass cylinder, 0.4 g of formulations 1 is sprayed onto the test cockroaches. Thirty (30) seconds after spraying formulation 1, the plastic container containing the cockroaches was removed from the glass container. The number of the test cockroaches at 20 minutes after spraying formulation 1 was observed for the knockdown effect thereof. All of the test cockroaches were then transferred to a separate sanitary plastic container (200 ml), and food as well as water was provided. The mortality of the cockroaches was observed 3 days after the formulation application.

Similarly, the 0.4 g of said formulations 2 and 3 and the comparative formulation was sprayed, respectively, onto 10 adult German cockroaches.

Each of the tests above with said formulations 1 to 3 and the comparative formulation was conducted 2 more times. The results with each of said formulations 1 to 3 and comparative formulations are averaged, respectively, as shown in Table 3.

TABLE 3

| | present compound:NMP weight to weight ratio | knockdown rate at 20 minutes after spraying (%) | mortality rate (%) |
| --- | --- | --- | --- |
| aerosol formulation 1 | 1:3 | 43 | 83 |
| aerosol formulation 2 | 1:10 | 83 | 93 |
| aerosol formulation 3 | 1:40 | 100 | 97 |
| comparative aerosol formulation 1 | not applicable | 10 | 53 |

NMP: N-methyl-2-pyrrolidone

What is claimed is:

1. A arthropod-controlling aerosol composition, comprising:
   (a) a propellant;
   (b) 1-methyl-2-nitro-3-[(3-tetrahydrofuryl)methyl] guanidine and
   (c) N-methyl-2-pyrrolidone;
   wherein a weight to weight ratio of said 1-methyl-2-nitro-3-[(3-tetrahydrofuryl)methyl]guanidine to said N-methyl-2-pyrrolidone is at an effective weight to weight ratio for controlling arthropods.

2. The arthropod-controlling aerosol composition according to claim 1, wherein the weight to weight ratio of 1-methyl-2-nitro-3-[(3-tetrahydrofuryl)methyl]guanidine to N-methyl-2-pyrrolidone is from 2:1 to 1:999.

3. The arthropod-controlling aerosol composition according to claim 1 or 2, wherein the propellant comprises at least 30% by weight of dimethyl ether, wherein said weight percentage is based on the total weight of the provided propellant.

4. An arthropod-controlling method comprising applying to an arthropod or to a habitat of an arthropod, an effective amount for controlling arthropods of the arthropod-controlling aerosol composition of claim 1.

5. The arthropod-controlling aerosol composition according to claim 1, comprising:
   (a) the propellant;
   (b) 0.01 to 10% by weight of 1-methyl-2-nitro-3-[(3-tetrahydrofuryl)methyl]guanidine and
   (c) 0.0005 to 30% by weight of N-methyl-2-pyrrolidone,
   wherein said weight percentages are based on the total weight of the provided arthropod-controlling aerosol composition and the weight to weight ratio of said 1-methyl-2-nitro-3-[(3-tetrahydrofuryl)methyl] guanidine to said N-methyl-2-pyrrolidone is at the weight to weight ratio effective for controlling arthropods.

6. The arthropod-controlling aerosol composition according to claim 1, wherein the weight to weight o of said 1-methyl-2-nitro-3-[(3-tetrahydrofuryl) methyl]guanidine to said N-methyl-2-pyrrolidone is 2:1 to 1:999.

* * * * *